United States Patent
Kitano et al.

[11] Patent Number: 5,914,348
[45] Date of Patent: Jun. 22, 1999

[54] SUBSTANCE FA-70D, PROCESS FOR PRODUCING THE SAME, AND USES THEREOF

[75] Inventors: Shizuo Kitano; Toru Sasaki; Kenichiro Yoshida; Toshio Otani, all of Tokushima, Japan; Lei Yu; Yun Wu, both of Beijing, China; Nobuhiko Katsunuma, Tokushima, Japan

[73] Assignee: Taiho Pharmaceutical Co., Ltd., Tokyo, Japan

[21] Appl. No.: 08/930,606

[22] PCT Filed: Feb. 20, 1997

[86] PCT No.: PCT/JP97/00472

§ 371 Date: Oct. 14, 1997

§ 102(e) Date: Oct. 14, 1997

[87] PCT Pub. No.: WO97/31122

PCT Pub. Date: Aug. 28, 1997

[30] Foreign Application Priority Data

Feb. 21, 1996  [JP]  Japan ................................ 8-033523

[51] Int. Cl.$^6$ .................................................. A01N 37/12
[52] U.S. Cl. ............................................ 514/563; 562/439
[58] Field of Search ............................. 562/439; 514/563

[56] References Cited

FOREIGN PATENT DOCUMENTS 7-123995  5/1995  Japan .
8-3188    1/1996  Japan .
8-151394  6/1996  Japan .

*Primary Examiner*—Brian M. Burn
*Assistant Examiner*—Brian J. Davis
*Attorney, Agent, or Firm*—Nikaido Marmelstein Murray & Oram, LLP

[57] ABSTRACT

Substance FA-70D which has the following formula (1), or its salt, a method for its production, a pharmaceutical composition comprising the compound as an active ingredient, a method of treating osteoporosis which comprises administering the compound, use of the compound as a drug, and a microorganism capable of producing Substance FA-70D are disclosed. This compound has specific inhibitory activity against cathepsin series proteases and is of value as a therapeutic drug for various diseases, particularly osteoporosis, with which these enzymes are associated.

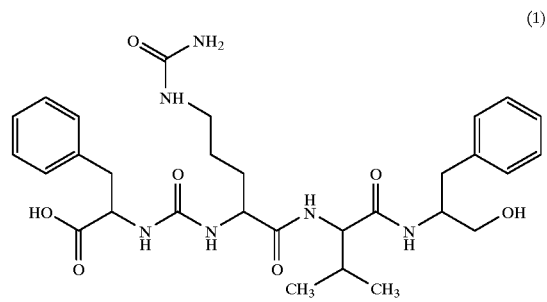

(1)

10 Claims, 2 Drawing Sheets

SUBSTANCE FA-70D, PROCESS FOR PRODUCING THE SAME, AND USES THEREOF

This is a national phase application of PCT/JP97/00472, which was filed on Feb. 20, 1997, under 35 U.S.C. §371.

TECHNICAL FIELD

The present invention relates to a novel Substance FA-70D, which has protease inhibitory activity and is useful as a medicine or to a salt thereof.

BACKGROUND ART

As a group of enzymes produced intracellularly, cathepsin series proteases (cathepsin B, cathepsin L, cathepsin H, etc.) are discharging a variety of physiological functions both intracellularly and extracellularly. For example, it is thought that intracellularly those enzymes are involved in the processing of proteins, decomposition of unwanted proteins, and apoptosis, while extracellularly they are associated with the decomposition of extracellular matrices such as degradation of bone matrix collagen and digestion of infecting bacteria.

Cathepsin L, in particular, is known to have very strong collagen degrading activity and it has been demonstrated in experimental animals, too, that inhibitors of cathepsin L exhibit marked inhibitory effects on the decomposition of bone collagen. Any substance that inhibits cathepsin L specifically is considered to be a promising drug for the therapy of osteoporosis (FEBS Letters, 269 (1), 189–193, 1990). Moreover, such a specific inhibitor of cathepsin L is considered to be a promising drug for the therapy of hypercalcemia.

Cathepsin B is an enzyme which is said to be etiologically associated, in a large measure, with inflammations, cancer metastases, myodystrophy and the like. Recent years have witnessed an increasing number of reports pointing out the correlation between the malignancy of cancer, such as metastasis and invasion, and cathepsin B activity (Cancer Research, 52, 3610–3614, 1992).

For treating diseases associated with cathepsin series proteases, specific inhibitors of those enzymes are needed today but no satisfactory substance has been discovered as yet. Particularly, there is not available a specific inhibitor of the cathepsin associated with bone resorption in osteoporosis.

The present invention has for its object to produce a substance having excellent cathepsin inhibitory activity by utilizing microorganisms.

DISCLOSURE OF THE INVENTION

The inventors of the present invention isolated a large number of microorganisms from the natural soil and screened them for those substances, among metabolites they produce, which would inhibit cathepsin series proteases. As a result, the inventors discovered a substance having cathepsin series protease inhibitory activity in cultures of a strain of microorganism belonging to Actinomycetes, designated FA-70 strain, isolated the substance, and determined its physicochemical properties and structure. The present invention has been developed on the basis of the findings.

As compounds produced by microorganisms and structurally resembling the compound of the present invention, there have been reported Mer-N5075A (Japanese Unexamined Patent Application No.100588/1994; The Journal of Antibiotics, 46, 1622–1624, 1993), α-MAPI and β-MAPI (Agricultural and Biological Chemistry, 43, 243–250, 1979; Tetrahedron Letters, (7), 625–628, 1979), and GE20372 Factor A and B (The Journal of Antibiotics, 48, 332–334, 1995). However, Substance FA-70D of the present invention is a novel compound structurally corresponding to a citrulline molecule linked by peptide bonding. The compound of the present invention is of value as a cathepsin L inhibitor or a medicine such as a therapeutic drug for osteoporosis.

The present invention, therefore, is directed to Substance FA-70D of the following formula (1) or a salt thereof.

(1)

In another aspect, the present invention is directed to a process for producing Substance FA-70D or a salt thereof which comprises cultivating a strain of microorganism belonging to the genus Streptomyces and capable of producing said Substance FA-70D in a culture medium to cause the strain to elaborate and accumulate the substance in the culture broth and harvesting the substance from said broth.

In further aspects, the present invention is directed to a medicine, a therapeutic drug for osteoporosis or a cathepsin L inhibitor, comprising said Substance FA-70D or a salt thereof.

The present invention is further directed to a pharmaceutical composition comprising said Substance FA-70D or a salt thereof and a pharmaceutically acceptable carrier therefor.

The present invention is further directed to a method of treating osteoporosis which comprises administering an effective amount of said Substance FA-70D or a salt thereof to a patient.

The present invention is directed, in a still another aspect, to use of said Substance FA-70D or a salt thereof for a medicine.

The present invention is further directed to microorganisms capable of producing said Substance FA-70D.

BEST MODE OF CARRYING OUT THE INVENTION

The salt of compound of formula (1) according to the present invention is not particularly limited but is preferably a base salt available upon reaction with a pharmaceutically acceptable basic compound. The base salt mentioned above includes salts with alkali metal carbonates such as sodium carbonate, potassium carbonate, etc., salts with alkali metal hydrogencarbonates such as sodium hydrogencarbonate, potassium hydrogencarbonate, etc., salts with alkali metal hydroxides such as sodium hydroxide, potassium hydroxide, etc., salts with alkali metals such as sodium, potassium, etc., salts with alkaline earth metals such as magnesium, calcium, etc., salts with ammonia, salts with amines such as methylamine, dimethylamine, triethylamine, cyclohexylamine, piperidine, etc., and salts with basic amino acids such as arginine and lysine.

Substance FA-70D of the above formula (1) includes optical isomers, therefore the isomers and mixtures thereof also fall within the scope of the invention.

Substance FA-70D of formula (1) or a salt thereof may be anhydrous or may have been appropriately hydrated. It may also be crystalline, powdery, or amorphous.

Physicochemical properties of Substance FA-70D are as follows.

Figure 1:
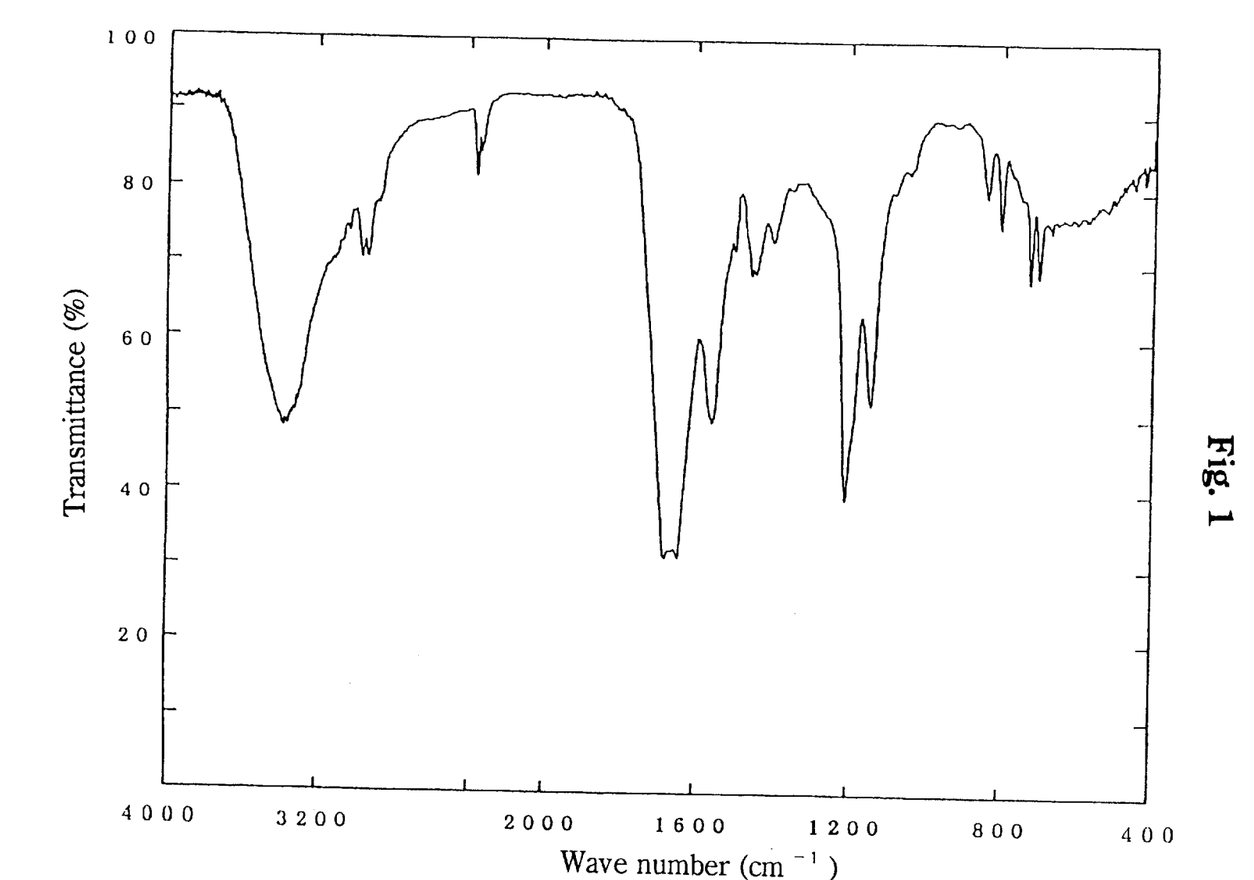
FIG. 1 shows an infrared absorption spectrum of the substance of the invention as obtained in Example 1.
Figure 2:
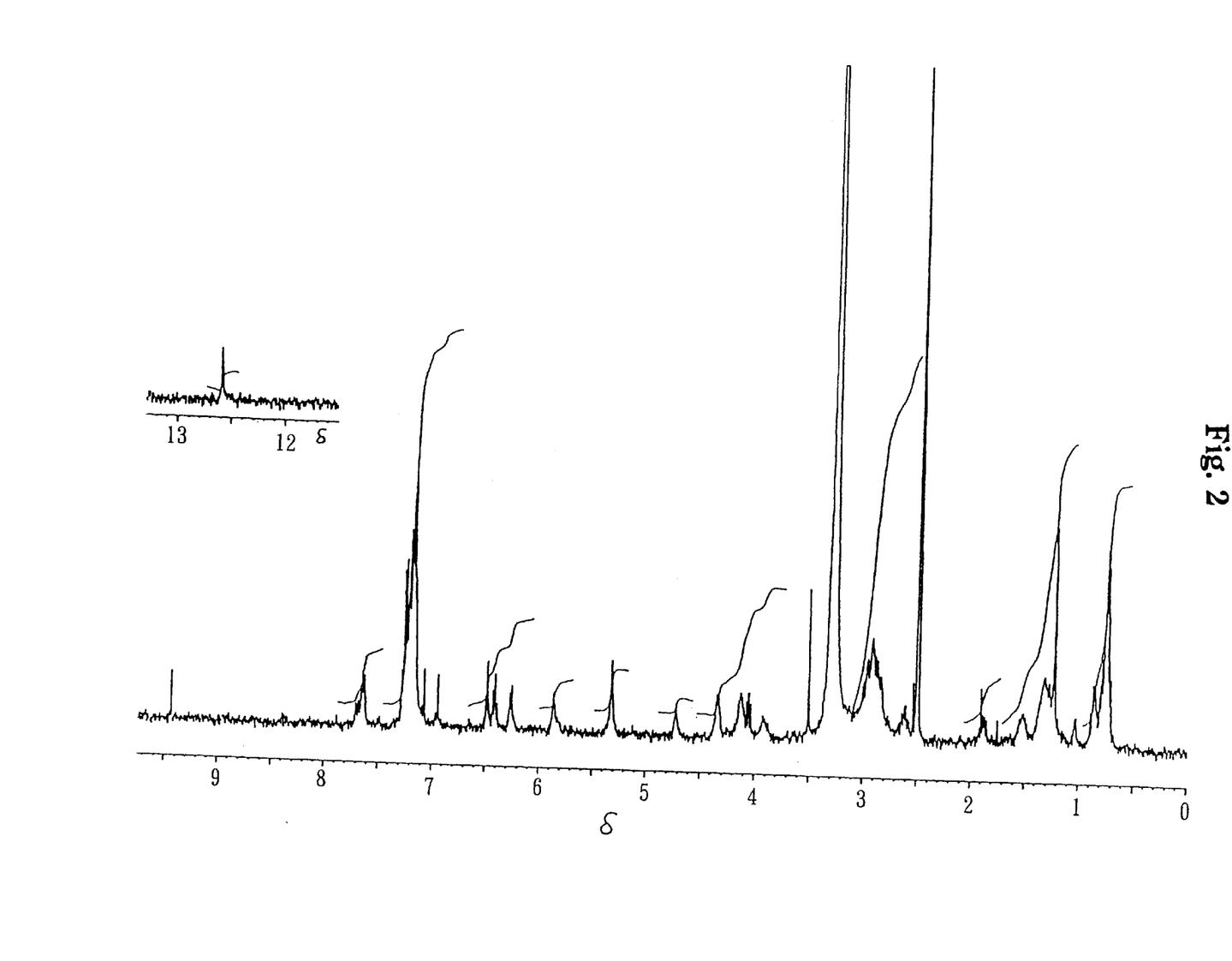
FIG. 2 shows a $^1$H-NMR spectrum of the substance of the invention as obtained in Example 1.

(1) Appearance: white powders
(2) Empirical formula: $C_{30}H_{42}N_6O_7$ (M) [high-resolution fast atomic bombardment mass spectrometry: Found 599.3181; calculated for $C_{30}H_{43}N_6O_7$ (M+H) 599.3193]
(3) Molecular weight: 598.701 (fast atomic bombardment mass spectrometry)
(4) Infrared absorption spectrum: KBr disk method νmax ($cm^{-1}$): 3375, 2965, 2935, 1675–1640, 1555, 1455, 1400, 1205, 1140, 840, 805, 725, 700. (FIG. 1)
(5) Nuclear magnetic resonance spectrum: the 400 MHz $^1$H-NMR spectrum in dimethylsulfoxide-$d_6$ (DMSO-$d_6$) at 30° C. is shown in FIG. 2. The chemical shifts are presented in Table 1.

TABLE 1

| Position | Chemical shift (δ) |
|---|---|
| COOH-Phe | 12.59 1H, br. s |
| NH-APP | 7.65 1H, d, 8 Hz |
| NH-Val | 7.64 1H, d, 8 Hz |
| Ar-Phe, APP | 7.13–7.28 10H, m |
| NH-Cit | 6.42 1H, d, 8 Hz |
| NH-Phe | 6.26 1H, d, 8 Hz |
| ε-Cit | 5.86 1H, m |
| CONH$_2$-Cit | 5.32 2H, br. s |
| CH$_2$OH-APP | 4.72 1H, m |
| α-Phe | 4.35 1H, m |
| α-Cit | 4.13 1H, m |
| α-Val | 4.06 1H, m |
| α-APP | 3.93 1H, m |
| β-Phe | 2.99 1H, m |
| γ-Cit | 2.92 1H, m |
| β-Phe | 2.87 1H, m |
| β-APP | 2.86 1H, m |
| β-APP | 2.62 1H, m |
| β-Val | 1.88 1H, m |
| CH$_2$OH-APP | 3.24–3.35 2H, m |
| β-Cit | 1.54 1H, m |
| β-Cit | 1.37 1H, m |
| γ-Cit | 1.33 2H, m |
| γ-Val | 0.76 3H, d, 7 Hz |
| γ-Val | 0.75 3H, d, 7 Hz |

Phe: phenylalanine
Cit: citrulline
Val: valine
APP: 2-amino-3-phenylpropanol (6) Solubility: readily soluble in methanol and dimethylsulfoxide and slightly soluble in ethanol. Practically insoluble in chloroform, acetone, ethyl acetate, ether, and hexane.
(7) Color reactions:
  Ehrlich reaction: positive
  Sakaguchi reaction and Ninhydrin reaction: negative
(8) Melting point: 157–158° C.
(9) Specific rotation: $[\alpha]_D^{20}=8.71°$ (c=3.56 mg/ml, methanol)
(10) High performance liquid chromatography: a peak at a retention time ($t_R$) of 5.8 min. under the following conditions.
  Column: Inertsil ODS-2, 5 μm (4.6 mm I.D.×150 mm, GL Science)
  Mobile phase: acetonitrile/trifluoroacetic acid/water (35:0.05:65, v/v/v)
  Flow rate: 1 ml/min.
  Detection: 210 nm (0.04 a.u.f.s.)

Substance FA-70D of the present invention can be produced by cultivating a strain of microorganism capable of producing the substance of the invention (hereinafter referred to as a substance FA-70D-producing strain) under appropriate conditions, typically under the following conditions. The substance FA-70D-producing strain includes strains of microorganisms belonging to the genus Streptomyces.

The present invention encompasses said Substance FA-70D and salts thereof which can be obtained by cultivating a strain of microorganism of the genus Streptomyces and recovering the culture broth.

As an example of said strain of microorganism belonging to the genus Streptomyces, there can be mentioned Streptomyces sp. FA-70 strain. This strain is a Streptomyces strain which the inventors of the present invention isolated from soil in Chéngdé, hébei, the Peoples Republic of China and has been deposited with National Institute of Bioscience and Human-Technology Agency of Industrial Science and Technology (Higashi 1-chome 1–3, Tsukuba-shi, Ibaraki, Japan) on Jul. 31, 1995 under the designation of microorganism: Strain FA-70 (as designated by the depositor for identification) and the accession number of FERM BP-5183.

The microbiological characteristics of the strain FA-70D investigated in accordance with the method described in International Journal of Systematic Bacteriology, 16 (3), 313–340, 1960 are as follows.

(a) Morphology

This strain was grown on Medium No. 4 (ISP 4) at 27° C. for 13 days according to the International Streptomyces Project (ISP). The results of observation are as follows.

Branching of sporulating hyphae: Simple branching
Form of sporulation: Spirales, spore form is cylindrical shape.
Number of spores: 10 to 50 or more spores
Spore surface: Smooth
Size of spore: 0.5–0.6×0.8–0.9 μm
Presence of flagellate: Not present
Presence of sporangia: Not present
Attachment site of sporophores: Aerial mycelium
Possession of sclerotium-forming ability: No possession (b) Cultural Characteristics on Various Media Cultural characteristics of strain FA-70D on various media are shown in Table 2. Taxonomic colors were indicated in accordance with The Japan Color Research Institute (ed.), Standard Color Chart A, 1981. Incidentally, more detailed colors were additionally given in parentheses in terms of color codes in accordance with The Color Harmony Manual (4th edition, 1958) published by Container Corporation of America.

TABLE 2

| Medium | Color of aerial mycelium | Color of substrate mycelium | Production of soluble pigment | Reverse color of colony |
|---|---|---|---|---|
| Sucrose nitrate agar | Dark yellow (2ie) ~ olive (2lg) ~ grayish olive (2ig, 2nl) | Pale yellowish brown (3ie) | Not produced | Pale yellowish brown |
| Glucose asparagine agar | White ~ bright olive gray (g) ~ olive gray (i) | Pale yellow ~ dull yellow (2gc) | Faint yellow | Light yellow ~ pale yellow |
| Glycerin asparagine agar (ISP-5) | Yellowish white ~ grayish olive (2nl) | Light yellow ~ pale yellowish brown (3ng) | Not produced | Pale yellow ~ pale yellowish brown (3ie) |
| Starch inorganic salt agar (ISP-4) | Bright olive gray (i) ~ dark olive (n) | Light yellow ~ pale yellowish brown | Not produced | Light yellow ~ pale yellowish brown |
| Tyrosine agar (ISP-7) | Yellowish white ~ light beige ~ gray (f) | Pale yellowish brown (3ie) | Not produced | Pale yellowish brown (3ie) |
| Oatmeal agar (ISP-3) | Yellowish white ~ yellowish gray ~ grayish olive (2nl) | Light yellow ~ pale yellowish brown (3ie) ~ yellowish brown (3ng) | Not produced | Light yellow ~ yellowish brown (3ng), deep yellowish brown (3ni) |
| Yeast extract malt extract agar (ISP-2) | Yellowish white ~ bright olive-gray (g) ~ olive gray (i, 1) | Light yellow | Faint brown | Yellowish brown |
| Nutrient agar | Not formed | Light yellow | Faint brown | Light yellow |
| Bennet's agar | White ~ yellowish gray ~ bright olive-gray (g) ~ olive gray (i) | Pale yellowish brown (3ie) | Faint brown | Yellowish brown (3ng) |

(c) Physiological Characteristics

Temperature range for growth: good growth at 20–37° C.

Liquefaction of gelatin (glucose peptone gelatin medium, 27° C.): positive

Liquefaction of gelatin (simple gelatin medium, 20° C.): negative

Coagulation of milk (37° C.): negative

Peptonization of milk (37° C.): positive

Production of melanoid pigments: negative on tyrosine agar (ISP-7) and tryptone yeast extract medium(ISP-1); positive on peptone yeast extract iron agar (ISP-6).

Production of hydrogen sulfide (peptone yeast extract iron agar (ISP-6) supplemented with 0.5% yeast extract): positive Hydrolysis of starch (starch inorganic salt agar (ISP-4)): positive Reduction of nitrates (bouillon containing 1% of potassium nitrate, ISP-8): negative Decomposition of cellulose: negative (d) Utilization of Carbon Sources (Pridham & Gottlieb agar, ISP-9)

This strain grows well by utilizing D-glucose, D-xylose, inositol, soluble starch, dextrin, glycerol, and maltose. L-arabinose, sucrose, D-fructose, D-mannitol, L-rhamnose, raffinose, D-galactose, and salicin are not utilized.

(e) Chemotaxonomy

The whole cell was analyzed for acid hydrolyzates by thin-layer chromatography in accordance with the method described in The Society for Actinomycetes Japan (ed.), [Experimental Method for Identifying Actinomycetes], 62–70, 1985. As a result, LL-form of diaminopimellic acid was detected.

Based on the above bacteriological characteristics, particularly the formation of an aerial mycelium attached a large number of spore chains from the vegetative mycelium, the constituent amino acid of the cell wall is LL-diaminopimellic acid, and neither flagella nor sporangia are formed, it is evident that the strain belongs to the genus Streptomyces. Therefore, the strain was named Streptomyces sp. FA-70 strain.

Substance FA-70D of the present invention can be produced by cultivating a substance FA-70D-producing strain belonging to the genus Streptomyces in a culture medium to cause it to produce and accumulate Substance FA-70D in the culture broth and harvesting the substance from said broth. In more detail, the method includes cultivating a substance FA-70D-producing strain belonging to genus Streptomyces, such as said FA-70 strain or a mutant thereof, in a suitable medium, separating a crude extract containing the substance of the invention from the culture broth, and isolating and purifying Substance FA-70D from the crude extract.

Culture of said strain of microorganism is carried out in accordance with the ordinary cultural procedure but generally is preferably carried out aerobically in a fluid medium by shaking-culture process or aerobic spinner culture process.

As the culture medium, any medium can be employed that contains nutrient sources which the substance FA70D-producing strain can utilize and a variety of synthetic media and natural media can be utilized. The carbon source that can be used includes but is not limited to glucose, sucrose, fructose, glycerin, dextrin, starch, molasses, corn steep liquor, and organic acids, and those sources can be used alone or in combination. The nitrogen source that can be used includes organic nitrogeneous substances such as Pharma media, peptone, meat extract, yeast extract, soybean meal, casein, amino acids, urea, etc. and inorganic nitrogenous substances such as sodium nitrate, ammonium sulfate, etc. Those substances may also be used alone or in combination. Where necessary, the medium may be supplemented with sodium salts, potassium salts, magnesium salts, phosphates, and heavy metal salts in suitable amounts. When copious foaming is encountered in the course of culture, there can be added to the medium an antifoamer such as vegetable oils, e.g. soybean oil, linseed oil, etc., higher alcohols, e.g. octadecanol, tetradecanol, heptadecanol, etc., and various silicon compounds.

The pH of the medium is preferably controlled within the neutral region. The cultivation temperature should be maintained within the range suitable to growth of the substance FA-70D-producing strain, i.e. generally 20–37° C., and preferably around 25–30° C. The cultivation time is preferably 2–6 days for both liquid shaking culture and aerobic agitating-culture.

The various incubation conditions mentioned above can be suitably modified according to the kind and characteristics of the microorganism used, external conditions and the like, and optimum conditions may be selected from and controlled within the above ranges depending thereon.

Separation of a crude extract containing Substance FA-70D from the culture broth can be achieved by the ordinary procedure for harvesting fermentation products. For example, solvent extraction, partition chromatography, adsorption chromatography, etc. can be used singly or in a suitable sequence and combination. Thus, since the Substance FA-70D elaborated in the course of culture is mostly secreted into the medium, the culture broth is filtered or centrifuged to separate the liquid fraction containing Substance FA-70D from the solid cellular fraction. Substance FA-70D in the obtained liquid fraction is then adsorbed on Diaion HP-20 resin (Mitsubishi Kasei Corporation). After the resin is rinsed with purified water, Substance FA-70D is eluted from the resin using methanol and the solvent is then distilled off under reduced pressure to provide a crude concentrate containing Substance FA-70D. To this crude concentrate is added n-butanol to transfer Substance FA-70D into the organic solvent and the solvent is then removed off under reduced pressure. The residue is washed with ethyl acetate and the solvent is then distilled away under reduced pressure to provide the crude extract containing Substance FA-70D.

The Substance FA-70D can be isolated and purified from the above crude extract by the routine procedure for the isolation and purification of low molecular weight peptides, e.g. adsorption chromatography on active charcoal, Diaion HP-20, ionic adsorbent resins, etc. and reversed phase chromatography using ODS-bonded silica gel or the like. Among those techniques, Diaion HP-20 chromatography using a mixture of methanol and water (pH 2.0) as eluent and reversed phase chromatography using a mixture of acetonitrile and trifluoroacetic acid as eluent are particularly useful. Moreover, when further purification is needed, the above chromatographic procedure can be repeated or carried out in combination with gel filtration chromatography using Sephadex LH-20 (Pharmacia) and, as eluent, methanol. By the above procedure, a high purity grade of Substance FA-70D can be obtained.

For identification of Substance FA-70D during the purification procedure, the assay of the enzymatic activity of papain or cathepsin L, which is inhibited by the substance, and the detection by high performance liquid chromatography can be advantageously carried out in combination.

The specific procedure for assaying such enzymatic activity is described in Examples and Test Examples.

Substance FA-70D or salt of the invention inhibits cathepsin L, thus substantiating its efficacy as a therapeutic drug for osteoporosis and hypercalcemia.

To use the above purified Substance FA-70D in the form of a pharmaceutical composition, it can be processed into a suitable dosage form according to the intended application. The dosage form includes oral dosage forms such as tablets, coated tablets, pills, powders, granules, fine granules, capsules, solutions, suspensions, emulsions, etc. and parenteral dosage forms such as injections, suppositories, ointments, plasters, aerosols, etc. Those dosage forms can be manufactured by the routine pharmaceutical procedures well known in the art.

The carrier for tablets includes various excipients such as lactose, sucrose, sodium chloride, glucose, urea, starch, calcium carbonate, kaolin, crystalline cellulose, silicic acid, etc., binders such as simple syrup, glucose solution, starch solution, gelatin solution, carboxymethylcellulose, shellac, methylcellulose, potassium phosphate, polyvinylpyrrolidone, etc., disintegrators such as desiccated starch, sodium alginate, agar powder, laminarin powder, sodium hydrogencarbonate, calcium carbonate, polyoxyethylene sorbitan fatty acid esters, sodium lauryl sulfate, stearyl monoglyceride, starch, lactose, etc., disintegration inhibitors such as sucrose, stearic acid, cacao butter, hydrogenated oil, etc., absorption promoters such as quaternary ammonium base, sodium lauryl sulfate, etc., humectants such as glycerin, starch, etc., adsorbents such as starch, lactose, kaolin, bentonite, colloidal silica, etc., and lubricants such as purified talc, stearic acid salts, boric acid powder, polyethylene glycol, etc. Where necessary, such tablets can be further processed into coated tablets using an ordinary coating film, for example dragees, gelatin-coated tablets, enteric tablets, film-coated tablets, etc., and can be double-layer tablets, multiple-layer tablets, etc.

For the manufacture of pills, various excipients such as glucose, lactose, starch, cacao butter, hydrogenated vegetable oil, kaolin, talc, etc., binders such as gum arabic powder, gum tragacanth powder, gelatin, etc., and disintegrators such as laminarin, agar, etc. can be used as the carrier.

Capsules can be manufactured in the conventional manner, i.e. by mixing the compound of the invention with the above-mentioned carrier and filling the mixture in hard gelatin capsule shells or soft capsule shells.

As to liquid preparations for oral administration, solutions, syrups, and elixirs can be manufactured by adding a corrigent, a buffer, a stabilizer, etc. to the active ingredient of the invention in the routine manner. The corrigent that can be used includes sucrose, orange peel, citric acid, tartaric acid, etc. The buffer that can be used includes but is not limited to sodium citrate, and the stabilizer includes gum tragacanth, gum arabic, and gelatin, among other substances.

For use as injections, solutions, emulsions or suspensions are preferably sterilized and made isotonic to the blood. The diluent that can be used for the manufacture of such injections includes water, ethyl alcohol, macrogols, propylene glycol, ethoxylated isostearyl alcohol, polyoxylated isostearyl alcohol, and polyoxyethylene sorbitan fatty acid esters, among others. In this procedure, the pharmaceutical composition can be supplemented with a sufficient amount of sodium chloride, glucose, or glycerin to render it isotonic. It is also possible to add a pH control agent, a buffer, a stabilizer, a local anesthetic, etc. as the carrier additives to provide injections for intravenous, intramuscular, subcutaneous, intradermal, or intraperitoneal administration. The pH control agent or buffer includes but is not limited to sodium citrate, sodium acetate, and sodium phosphate. The stabilizer includes sodium pyrosulfite, ethylenediaminetetracetic acid, thioglycolic acid, and thiolactic acid, among other substances. The local anesthetic that can be used includes but is not limited to procaine hydrochloride and lidocaine hydrochloride.

Suppositories can be manufactured by adding a suppository base, optionally a surfactant, to the active ingredient of the invention in the per se known manner. The base that can be used includes oleagenous bases such as macrogols, lanolin, cacao butter, fatty acid triglycerides, Witepsol® (Dynamit Nobel), etc.

In the manufacture of ointments, the conventional carriers such as an ointment base, a stabilizer, a wetting agent, and a preservative are added, as required, to the compound of the invention and the mixture and formulation are processed in the routine manner. The ointment base that can be used includes but is not limited to liquid paraffin, white petrolatum, bleached beeswax, octyldodecyl alcohol, and paraffin. The preservative includes methyl p-hydroxybenzoate, ethyl p-hydroxybenzoate, and propyl p-hydroxybenzoate, to name but a few.

The plasters can be manufactured by coating a conventional support with said ointment, paste, cream, or gel in the routine manner. The support that can be used with advantage includes but is not limited to woven or nonwoven fabrics of cotton, spun rayon yarn, or chemical fiber, films of flexible polyvinyl chloride, polyethylene, polyurethane, etc., and foamed sheets of such materials.

Where necessary, the dosage forms described above may be supplemented with other additives such as colorants, preservatives, perfumes, flavors, sweeteners, etc. and other medicinally active ingredients.

The proportion of the compound of the invention in the pharmaceutical composition of the invention is not so critical and can be selected liberally from a broad range but, generally speaking, is preferably 1–70 weight %.

There is no particular limitation on the mode of administration of the pharmaceutical composition. Thus, a suitable mode can be selected according to the particular dosage form, the patient's age, sex, and other factors, and the severity of disease. For example, tablets, pills, solutions, suspensions, emulsions, granules, and capsules are administered orally. Injections are administered, either alone or in admixture with an ordinary infusion such as a glucose solution or an amino acid infusion, by the intravenous route. If necessary, injections can be administered alone intramuscularly, intradermally, subcutaneously or intraperitonally. Suppositories are administered into the rectrum. Ointments are applied to the skin or the mucosa in the oral cavity.

The amount of the active compound of the invention which is to be formulated in each dosage unit of the above forms cannot be defined in general terms, for it depends on the clinical condition of the patient and the dosage form. Generally, however, the amount in each unit dosage form is preferably about 1–1000 mg for oral preparations, about 0.1–500 mg for injections, and about 5–1000 mg for suppositories.

The daily dose of the active compound in any of the above dosage forms can be judiciously selected according to the patient's condition, body weight, age, sex, and other conditions. Usually, however, the daily dose for an adult patient may be about 0.1–1000 mg/kg and preferably about 1–100 mg/kg. This dosage can be administered once a day or in about 2–4 divided doses.

EXAMPLES

The following working examples and test examples are merely intended to describe the invention in further detail and should by no means be construed as defining the scope of the invention.

Example 1

Production of Substance FA-70D of the Invention
(a) Culture Process

An Erlenmeyer flask (500 ml) was charged with 100 ml of a medium (pH 7.2) composed of 0.5% glucose, 2.4% soluble starch, 0.3% beef extract, 0.5% yeast extract, 0.5% peptone, 0.4% corn steep liquor, 0.002% cobalt chloride, and 0.4% calcium carbonate, and after sterilization, was inoculated with a loopful of Streptomyces sp. FA-70 strain (accession number FERM BP-5183). The flask was then incubated at 27° C. on a rotary shaker for 3 days (220 rpm., 7 cm throw).

Then, a medium (pH 7.0) composed of 2.0% glycerol, 2.0% dextrin, 0.3% yeast extract, 1.0% soyton, 0.2% ammonium sulfate, and 0.2% calcium carbonate was distributed into conical flasks of 500 ml capacity, 100 ml per flask, and after sterilization (121° C., 15 min.), the above seed culture was added at the level of 2% (v/v) to each flask. The inoculated flasks were incubated at 27° C. on a rotary shaker for 3 days (220 rpm., 7 cm throw).

(b) Separation Process

The culture broth obtained by the above procedure (8.5 L, pH 6.1) was harvested, centrifuged (3000 rpm, 15 min.), and filtered. The culture filtrate thus obtained was adjusted to pH 8.0 with 1N sodium hydroxide/water, and Diaion HP-20 (Mitsubishi Kasei Corporation) resin (850 ml) was added. After 1 hour of agitation, the resin was separated by filtration and then the resin was treated with methanol (4250 ml) while it was adjusted to pH 2.0 with 1 N-hydrochloric acid under stirring in order to elute Substance FA-70D. The above procedure was further repeated twice and the methanol extract was adjusted to pH 6.0 with 1 N-sodium hydroxide/water and centrifuged. The supernatant was concentrated under reduced pressure to provide a methanol-free aqueous solution containing Substance FA-70D. This aqueous solution was adjusted to pH 8.0 with 1 N-sodium hydroxide/water and extracted with the same volume (v/v) of n-butanol 3 times. The pooled n-butanol extract was concentrated under reduced pressure and the solid residue was rinsed with ethyl acetate (50 ml) 3 times and dried to provide a crude extract containing Substance FA-70D (7.2 g).

(c) Isolation and Purification Process

The above crude extract (4.2 g) was dissolved in methanol (84 ml) and the solution was centrifuged (3000 rpm, 15 min.) to separate the methanol-soluble fraction from the insoluble fraction. The insoluble fraction was further diluted with methanol (33 ml) and centrifuged to separate the methanol-soluble fraction from the insoluble fraction. The methanol-soluble fractions were pooled, diluted with water (2213 ml), and adjusted to pH 3.0 with 1 N-hydrochloric acid. The resulting precipitate was removed. The methanol-containing aqueous solution was adjusted to pH 7.0 with 1 N-sodium hydroxide/water and applied to a CM-Sephadex column (Pharmacia, CM-Sephadex C-25, H$^+$-form, 3.6 cm I.D.×30 cm). The non-absorbed fraction (column pass through fraction) containing Substance FA-70D was adjusted to pH 7.0 with 1 N-sodium hydroxide/water and applied to a DEAE-Sephadex column (Pharmacia, DEAE-Sephadex A-25, OH$^-$-form, 3.6 cm I.D.×30 cm). The column was rinsed with water and elution was carried out with 0.1 M sodium chloride. The obtained eluate was further applied to a Diaion HP-20 resin column (2 cm I.D.×15 cm long). After the column was rinsed with water, elution was carried out with 60% methanol/water (adjusted to pH 2.0 with diluted hydrochloric acid). The obtained eluate was concentrated under reduced pressure to provide a dry powder containing Substance FA-70D (240 mg).

Detection of active fractions containing Substance FA-70D in each stage was carried out by the assay of papain inhibitory activity (Biochemical Journal, 201, 189–198, 1982).

Thus, 0.5 ml of 400 mM sodium phosphate buffer (pH 6.8) containing 8 mM dithiothreitol and 4 mM tetrasodium ethylenediaminetetracetate, 0.8 ml of an enzyme solution containing 5 μM papain and 0.1% Brij 35 (polyoxyethylene (23) lauryl ether) (Wako Pure Chemical Ind.), and 0.2 ml of an aqueous solution containing a sample were preincubated at 40° C. for 10 minutes. Then, 0.5 ml of a 0.1% aqueous solution of dimethyl sulfoxide containing 20 μM carbobenzoxy-L-phenylalanyl-L-arginine-4-methylcoumaryl-7-amide was added and the mixture was incubated at 40° C. for 10 minutes. The enzymatic reaction was stopped by adding 2.0 ml of 100 mM sodium acetate buffer (pH 4.3) containing 100 mM sodium monochloroacetate and the intensity of fluorescence (F) was measured at an exciting wavelength of 350 nm and an emission wavelength of 458 nm. As a control, 0.2 ml of water was added in lieu of 0.2 ml of said aqueous solution of the sample and the intensity of fluorescence ($F_0$) at 458 nm was similarly measured. The enzyme inhibitory activity was calculated by means of the following formula.

Enzyme inhibitory activity $(\%) = F/F_0 \times 100$

The dry powder obtained was dissolved in methanol and the solution was applied to a gel filtration column (Pharmacia, Sephadex LH-20, 2 cm I.D.×127 cm). Elution was carried out with methanol. The active fractions were pooled and the solvent was removed to recover a dry powder (37 mg). This dry powder was dissolved in methanol and subjected to reversed phase high performance liquid chromatography with an Inertsil ODS-2 column (GL Science, 5 μm, 10 mm I.D.×250 mm) and, as a mobile phase, acetonitrile/trifluoroacetic acid/water (v/v/v, 35:0.05:65) at a flow rate of 4.0 ml/min. The active fractions were pooled and the organic solvent was distilled away under reduced pressure. The residual aqueous solution was lyophilized to provide Substance FA-70D as a white powder (11 mg).

The physicochemical properties of the Substance FA-70D thus obtained were as follows.

(1) Appearance: white powders
(2) Empirical formula: $C_{30}H_{42}N_6O_7$ (M) [high-resolution fast atomic bombardment mass spectrometry: Found 599.3181; calculated for $C_{30}H_{43}N_6O_7$ (M+H) 599.3193]
(3) Molecular weight: 598.701 (fast atomic bombardment mass spectrometry)
(4) Infrared absorption spectrum: KBr disk method νmax (cm$^{-1}$): 3375, 2965, 2935, 1675–1640, 1555, 1455, 1400, 1205, 1140, 840, 805, 725, 700. (FIG. 1)
(5) Nuclear magnetic resonance spectrum: the 400 MHz $^1$H-NMR spectrum in dimethylsulfoxide-$d_6$ (DMSO-$d_6$) at 30° C. is shown in FIG. 2. The chemical shifts are presented in Table 3.

TABLE 3

| Position | Chemical shift (δ) |
|---|---|
| COOH-Phe | 12.59 1H, br. s |
| NH-APP | 7.65 1H, d, 8 Hz |
| NH-Val | 7.64 1H, d, 8 Hz |
| Ar-Phe, APP | 7.13–7.28 10H, m |
| NH-Cit | 6.42 1H, d, 8 Hz |
| NH-Phe | 6.26 1H, d, 8 Hz |
| ε-Cit | 5.86 1H, m |
| CONH$_2$-Cit | 5.32 2H, br. s |
| CH$_2$OH-APP | 4.72 1H, m |
| α-Phe | 4.35 1H, m |
| α-Cit | 4.13 1H, m |
| α-Val | 4.06 1H, m |
| α-APP | 3.93 1H, m |

TABLE 3-continued

| Position | Chemical shift (δ) |
|---|---|
| β-Phe | 2.99 1H, m |
| γ-Cit | 2.92 1H, m |
| β-Phe | 2.87 1H, m |
| β-APP | 2.86 1H, m |
| β-APP | 2.62 1H, m |
| β-Val | 1.88 1H, m |
| CH$_2$OH-APP | 3.24–3.35 2H, m |
| β-Cit | 1.54 1H, m |
| β-Cit | 1.37 1H, m |
| γ-Cit | 1.33 2H, m |
| γ-Val | 0.76 3H, d, 7 Hz |
| γ-Val | 0.75 3H, d, 7 Hz |

Phe: phenylalanine
Cit: citrulline
Val: valine
APP: 2-amino-3-phenylpropanol (6) Solubility: readily soluble in methanol and dimethyl sulfoxide and slightly soluble in ethanol. Practically insoluble in chloroform, acetone, ethyl acetate, ether, and hexane.
(7) Color reactions:
   Ehrlich reaction: positive
   Sakaguchi reaction and Ninhydrin reaction: negative
(8) Melting point: 157–158° C.
(9) Optical rotation: $[\alpha]_D^{20} = -8.71°$ (c=3.56 mg/ml, methanol)
(10) High performance liquid chromatography: a peak at a retention time ($t_R$) of 5.8 min. under the following conditions.
   Column: Inertsil ODS-2, 5 μm (4.6 mm I.D.×150 mm, GL Science)
   Mobile phase: acetonitrile/trifluoroacetic acid/water (35:0.05:65, v/v/v)
   Flow rate: 1 ml/min.
   Detection: 210 nm (0.04 a.u.f.s.)

Test Example 1

Determination of the enzyme-inhibitory activity of Substance FA-70D.

The inhibitory activity against cathepsin L or cathepsin B was assayed by the method of A. J. Barrett et al. [Biochemical Journal, 201, 189–198, 1982]. The chymotrypsin- or trypsin-hibitory activity was assayed in accordance with the methods described in Tsuru, D. and Funatsu, M. (ed.), Seikagaku Jikkenho-Tanpakushitsu Bunkai Koso II [Methods of Biochemistry, Proteolytic Enzymes II], vol. 31, 7–14, 1993.

The method for assay of inhibitory activity against cathepsin B is as follows. Thus, 0.5 ml of 400 mM sodium phosphate buffer (pH 6.0) containing 8 mM dithiothreitol and 4 mM tetrasodium ethylenediaminetetracetate, 0.8 ml of an enzyme solution containing 5 μM cathepsin B and 0.1% Brij 35 (Wako Pure Chemical Ind.), and 0.2 ml of an aqueous solution of the compound of the invention were preincubated at 40° C. for 10 minutes. Then, 0.5 ml of a 0.1% aqueous solution of dimethyl sulfoxide containing 20 μM carbobenzoxy-L-phenylalanyl-L-arginine-4-methylcoumaryl-7-amide was added and the mixture was incubated at 40° C. for 10 minutes. The enzymatic reaction was then stopped by adding 2.0 ml of 100 mM sodium acetate buffer (pH 4.3) containing 100 mM sodium monochloroacetate. The intensity of fluorescence (F) was determined at an exciting wavelength of 350 nm and an emission wavelength of 458 nm. As a control, 0.2 ml of water was added in lieu of 0.2 ml of said aqueous solution of the compound of the invention and the intensity of fluorescence ($F_0$) at 458 nm was similarly measured. The enzyme inhibitory activity was calculated by means of the following formula.

Enzyme inhibitory activity (%)=$F/F_0 \times 100$

The inhibitory activity against cathepsin L was assayed as follows. Thus, except that cathepsin L was used in lieu of cathepsin B at the same concentration and the 400 mM sodium phosphate buffer was adjusted to pH 5.5, the above assay procedure for cathepsin B was otherwise repeated to determine the enzyme inhibitory activity.

The inhibitory activity against chymotrypsin was assayed in the following manner. Thus, 0.1 ml of 100 mM Tris-HCl buffer (pH 7.5), 0.15 ml of water, 0.01 ml of 5 ng/ml chymotrypsin/water, and 0.04 ml of an aqueous solution of the compound of the invention were preincubated at 37° C. for 5 minutes. Then, 0.1 ml of an aqueous solution containing 100 µM succinyl-L-leucyl-L-leucyl-L-valyl-L-tyrosine-4-methylcoumaryl-7-amide was added and the mixture was incubated at 37° C. for 20 minutes. The enzymatic reaction was stopped by adding 0.5 ml of 100 mM sodium acetate buffer (pH 4.3) containing 100 mM sodium monochloroacetate and the intensity of fluorescence (F) was measured at an exciting wavelength of 350 nm and an emission wavelength of 458 nm. As a control, 0.04 ml of water was added in lieu of 0.04 ml of said aqueous solution of the compound of the invention and the intensity of fluorescence ($F_0$) at 458 nm was similarly measured. The enzyme inhibitory activity was calculated by the following formula.

Enzyme inhibitory activity (%)=$F/F_0 \times 100$

The inhibitory activity against trypsin was measured as follows. Except that trypsin was used in lieu of chymotrypsin at the same concentration and benzoyl-L-leucyl-L-lysyl-arginine-4-methylcoumaryl-7-amide was used in lieu of succinyl-L-leucyl-L-leucyl-L-valyl-L-tyrosine-4-methylcoumaryl-7-amide at the same concentration, the above procedure for assaying the inhibitory activity against chymotrypsin was otherwise repeated and the enzyme inhibitory activity was calculated in the same manner as above.

The results are shown in Table 4.

TABLE 4

| Concentration of FA-70D (M) | Enzyme inhibitory activity (%) | | | |
|---|---|---|---|---|
| | Cathepsin B | Cathepsin L | Chymotrypsin | Trypsin |
| $10^{-6}$ | 85.5 | 93.5 | 99.9 | 43.3 |
| $10^{-7}$ | 23.7 | 72.0 | 97.6 | 14.0 |
| $10^{-8}$ | —1.0 | 15.1 | 70.7 | 9.4 |

It is clear from Test Example 1 that Substance FA-70D of the invention inhibits cathepsin L more strongly than cathepsin B and inhibits chymotrypsin more strongly than trypsin.

| Formulation Example 1 Capsules | |
|---|---|
| Substance FA-70D | 10 mg |
| Lactose | 50 mg |

| Formulation Example 1 Capsules (continued) | |
|---|---|
| Corn starch | 47 mg |
| Crystalline cellulose | 50 mg |
| Talc | 2 mg |
| Magnesium stearate | 1 mg |
| Per capsule | 160 mg |

According to the above recipe, capsules were manufactured by the routine procedure.

| Formulation Example 2 Injection | |
|---|---|
| Substance FA-70D | 5 mg |
| Distilled water for injection | q.s. |
| Per ampule | 5 ml |

According to the above recipe, an injection was manufactured by the routine procedure.

| Formulation Example 3 Suppositories | |
|---|---|
| Substance FA-70D | 20 mg |
| Witepsol W-35 (trademark of Dynamit Nobel) | 1380 mg |
| Per suppository | 1400 mg |

According to the above recipe, suppositories were manufactured by the routine procedure.

INDUSTRIAL APPLICABILITY

Substance FA-70D of the invention does strongly inhibit cathepsin series proteases and is of value as a therapeutic drug for various diseases associated with those enzymes, particularly osteoporosis.

What is claimed is:

1. Substance FA-70D which has the following formula (1) or a salt thereof.

(1)

2. A method of producing Substance FA-70D or its salt as defined in claim 1 which comprises cultivating a strain of microorganism belonging to the genus Streptomyces and capable of producing Substance FA-70D in a culture medium to cause it to produce and accumulate the substance in fermentation broth and harvesting the substance from said broth.

3. The method of producing Substance FA-70D or its salt according to claim 2 wherein the strain of microorganism is Streptomyces sp. FA-70 strain or a mutant thereof.

4. A medicine comprising Substance FA-70D or its salt as defined in claim 1 as an active ingredient.

5. The medicine according to claim 4 which is a cathepsin L inhibitor.

6. The medicine according to claim 4 which is a therapeutic drug for osteoporosis.

7. A pharmaceutical composition comprising an effective amount of Substance FA-70D or its salt as defined in claim 1 and a pharmaceutically acceptable carrier.

8. The pharmaceutical composition according to claim 7 which is for the therapy of osteoporosis.

9. A method of treating osteoporosis which comprises administering to a patient with an effective amount of Substance FA-70D or its salt as defined in claim 1.

10. A method for inhibiting a cathepsin series protease in a patient in need thereof, which method comprises administering an effective amount of Substance FA-70D or its salt as defined in claim 1 to said patient.

* * * * *